(12) United States Patent
Kalliomaki et al.

(10) Patent No.: US 7,792,648 B2
(45) Date of Patent: Sep. 7, 2010

(54) SYSTEM FOR DETERMINING PEDALLING EFFORT OF BICYCLE

(75) Inventors: Kalevi Kalliomaki, Espoo (FI); Jorma Honkala, Oulu (FI); Heikki Prokkola, Oulunsalo (FI); Mika Niemimaki, Haukipudas (FI)

(73) Assignee: Polar Electro Oy, Kempele (FI)

( * ) Notice: Subject to any disclaimer, the term of this patent is extended or adjusted under 35 U.S.C. 154(b) by 83 days.

(21) Appl. No.: 12/142,152

(22) Filed: Jun. 19, 2008

(65) Prior Publication Data

US 2009/0319203 A1    Dec. 24, 2009

(51) Int. Cl.
*G01L 1/00* (2006.01)
(52) U.S. Cl. ......................................... 702/44
(58) Field of Classification Search ............. 702/41–44; 73/862.621, 826
See application file for complete search history.

(56) References Cited

U.S. PATENT DOCUMENTS 5,167,159 A * 12/1992 Lucking ................. 73/862.451
5,257,540 A    11/1993 Bower et al.
6,199,021 B1    3/2001 Cote et al.

FOREIGN PATENT DOCUMENTS

| DE | 19646979 | 9/1998 |
|---|---|---|
| DE | 19905461 | 8/2000 |
| FI | 20051299 | 6/2007 |
| JP | 2000074761 | 3/2000 |

* cited by examiner

*Primary Examiner*—Drew A Dunn
*Assistant Examiner*—Stephen J Cherry
(74) *Attorney, Agent, or Firm*—Hoffmann & Baron, LLP

(57) ABSTRACT

A system determines pedaling effort of a bicycle and includes a first detector to generate a first sensor signal responsive to passage of a force transmission chain across a first frame-fixed point located in proximity to the force transmission trajectory of the force transmission chain, a second detector for generating a second sensor signal responsive to passage of a force transmission chain across a second frame-fixed point located in proximity to the force transmission trajectory of the force transmission chain, and a controller configured to receive the first and second sensor signals and configured to determine a first pedaling parameter proportional to tension of the force transmission chain by using the first and second sensor signal. A corresponding method for determining pedaling effort of a bicycle, and a computer program distribution medium including instructions for executing a computer process in a digital processor are also disclosed.

13 Claims, 5 Drawing Sheets

SYSTEM FOR DETERMINING PEDALLING EFFORT OF BICYCLE

BACKGROUND OF THE INVENTION

1. Field of the Invention

The invention relates to bicycles, especially measurements on performance associated with cycling.

2. Description of the Related Art

Due to a precise mechanical transmission system, a bicycle offers an excellent opportunity to measure performance characteristics, such as speed, distance and mechanical performance parameters associated with pedaling. The determination of the mechanical performance parameters often involves measurement of pedaling effort, such as pedaling force, pedaling power and pedaling speed.

There have been several efforts for developing pedaling measurement methods. Cote et al. (U.S. Pat. No. 6,199,021B1) has presented a power output determination method which is based on measurement of vibration frequency of a bicycle chain. There are also suggestions on applying strain gauges for measuring deformation of chain, cranks or force transmission axles.

Therefore, it is useful to consider alternatives for pedaling effort measurements.

SUMMARY OF THE INVENTION

In a first aspect of the invention, there is provided a system determining pedaling effort of a bicycle, comprising: a first detector for generating a first sensor signal responsive to passage of a force transmission chain across a first frame-fixed point located in the proximity of the force transmission trajectory of the force transmission chain; a second detector for generating a second sensor signal responsive to passage of a force transmission chain across a second frame-fixed point located in the proximity of the force transmission trajectory of the force transmission chain; and a controller configured to receive the first sensor signal and the second sensor signal and configured to determine a first pedaling parameter proportional to tension of the force transmission chain by using the first sensor signal and the second sensor signal.

In a second aspect of the invention, there is provided a method of determining pedaling effort of a bicycle, comprising: generating a first sensor signal responsive to passage of a force transmission chain across a first frame-fixed point located in the proximity of the force transmission trajectory of the force transmission chain; generating a second sensor signal responsive to passage of a force transmission chain across a second frame-fixed point located in the proximity of the force transmission trajectory of the force transmission chain; receiving the first sensor signal and the second sensor signal; and determining a first pedaling parameter proportional to tension of the force transmission chain by using the first sensor signal and the second sensor signal.

In another aspect of the invention, there is provided a computer program distribution medium comprising encoded instructions for executing a computer process in a digital processor, the computer process comprising: receiving a first sensor signal responsive to passage of a force transmission chain across a first frame-fixed point located in the proximity of the force transmission trajectory of the force transmission chain; receiving a second sensor signal responsive to passage of a force transmission chain across a second frame-fixed point located in the proximity of the force transmission trajectory of the force transmission chain; and determining a first pedaling parameter proportional to tension of the force transmission chain by using the first sensor signal and the second sensor signal.

BRIEF DESCRIPTION OF THE DRAWINGS

In the following, the invention will be described in greater detail by means of preferred embodiments with reference to the accompanying drawings, in which.

DETAILED DESCRIPTION OF THE PREFERRED EMBODIMENTS

Figure 1:
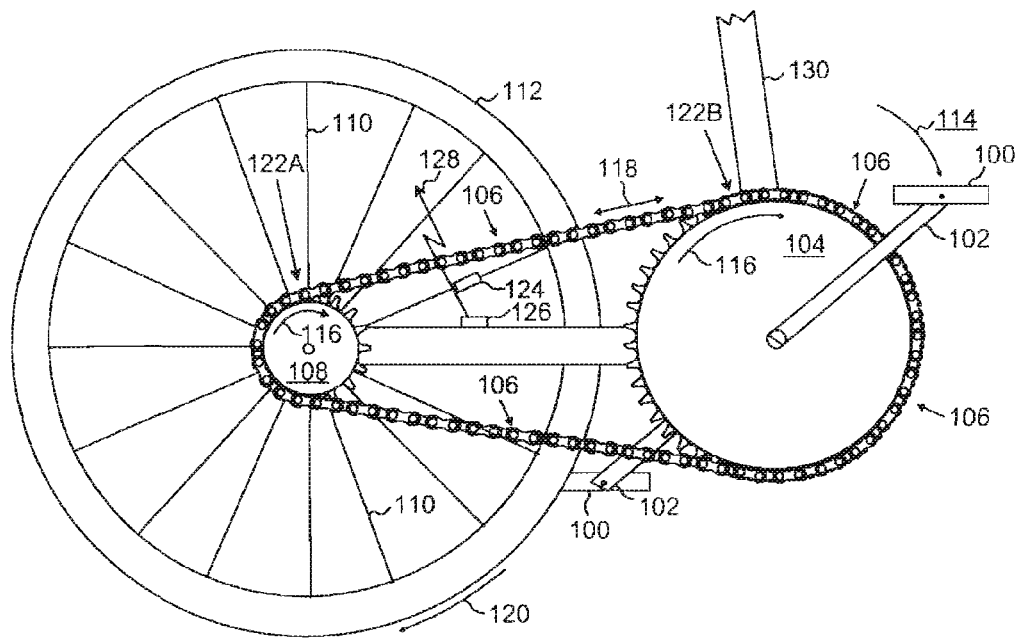
FIG. 1 shows a bicycle force transmission system according to an embodiment of the invention.

FIG. 1 shows a bicycle power transmission system comprising pedals 100, cranks 102, a front sprocket 104, a force transmission chain 106, a rear sprocket 108 and a drive wheel 112.

A cyclist directs pedaling force 114 to the pedals 100, thus resulting in a torque to the crank 102. The torque is transmitted to the front sprocket 104 which transforms the torque into tangential force 116. The tangential force 116 is transmitted to the force transmission chain 106 in a front force transmission contact point 122B via the teeth of the front sprocket 104.

The force transmission chain 106 forms an endless loop which transmits the tangential force 116 to the rear sprocket 108 in a rear force transmission contact point 122A and generates torque which is transmitted to the drive wheel 112 via spokes 110. The drive wheel 112 further transforms the torque into tangential force 120 which is transmitted to the ground, thus resulting in overall motion of the bicycle.

An essential role in the force transmission system is played by the force transmission chain 106 which transfers the tangential force 116 from the front sprocket 104 to the rear sprocket 108 and directs the force 118 into an appropriate direction. The force between the front force transmission point 122B and the rear force transmission contact point 122A results in uniform tension over the force transmission chain 106 between the transmission contact points 122A, 122B and characterizes an effort put into pedaling by the cyclist. The portion of the force transmission chain 106 between the front force transmission point 122B and the rear force transmission point 122A may also be referred to as force transmission trajectory.

The tension in the force transmission chain 106 results in deformation of the force transmission chain 106. A longitudinal deformation, i.e. the stretch of the force transmission chain 106 is proportional to the stretching force 118. The relationship between the stretch x and stretching force F may be written as $$F = k \times x + k' x^2 + k'' x^3, \quad (1)$$

wherein k, k" and k" are constants depending upon force transmission chain characteristics, such as mass and elastic properties. A typical stretch may exceed 4 millimeters at 1000 N force, thus providing a well detectable deformation.

The power transmitted by the force transmission chain 106 may be obtained from the stretching force and velocity $v_{ch}$ of the force transmission chain 106 as follows:

$$P = F \times v_{ch}. \quad (2)$$

The overall velocity of the bicycle V during cycling may be obtained from the following relation:

$$V = A_{RTR} \times v_c, \quad (3)$$

wherein $A_{RTR}$ is a rear transmission ratio and characterizes the circumference of the drive wheel 112 relative to that of the rear sprocket 108.

If the force transmission chain 106 is displaced from an equilibrium position in a direction that is perpendicular to the force transmission trajectory, the force transmission chain vibrates at a frequency which is proportional to the stretching force 118. Such a displacement may be generated when a moving pin of the force transmission chain 106 hits a tooth of the front sprocket 104. In harmonic approximation, the stretching force 118 is proportional to the square of the vibration frequency of the force transmission chain 106, and the pedaling power may be obtained from equation (2). However, the harmonic approximation may fail at large stretching forces 118, thus resulting in erroneous pedaling power.

The bicycle may further be equipped with a motion sensing system which may comprise a sensor unit 126 fixed to the bicycle frame and a detection element 124 fixed to a spoke 110. The motion sensing system may detect the rotation of the drive wheel or a front wheel, and the information 128 on the rotation may be transmitted to a bike computer or alike. The information 128 may be used in a bike computer for determining the speed of the bike.

The motion sensing system may also be implemented with acceleration sensor attached to the spoke 110, wherein the acceleration sensor may wirelessly communicate acceleration information to a bike computer or the like. In an embodiment of the invention, the passages of spokes are detected based on inductive or capacitive sensing without any elements added to the spokes.

In an embodiment of the invention, the velocity of the bike is calculated from the chain velocity by using equation 2 when the velocity of the force transmission chain 106 is known.

Figure 2:
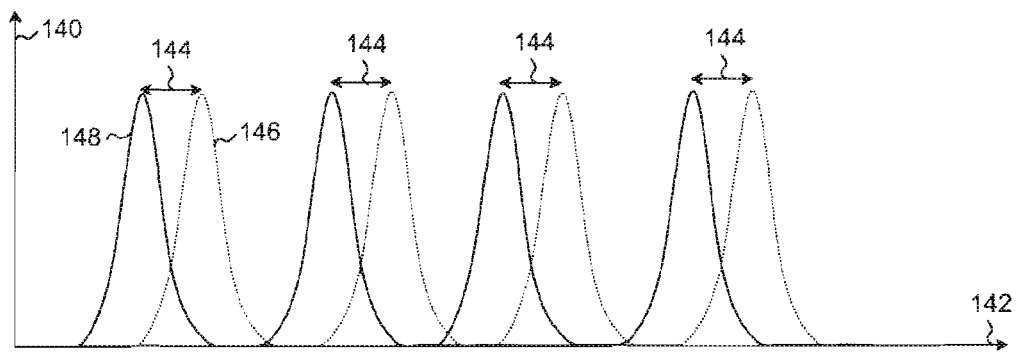
FIG. 2 shows a sensor signal characterizing the passage of a force transmission chain across a frame-fixed point according to an embodiment of the invention.
Figure 3:
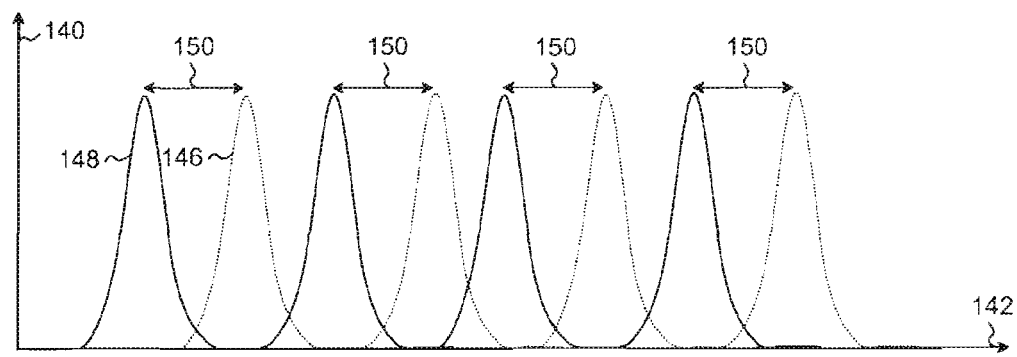
FIG. 3 shows a sensor signal characterizing the passage of a force transmission chain across a frame-fixed point according to an embodiment of the invention.

FIGS. 2 and 3 illustrate sensor signals 146, 148 which characterize the passage of the force transmission chain 106 in two frame-fixed points which are located along the force transmission trajectory. An x axis 142 illustrates time in arbitrary time units while a y axis 140 shows signal level in arbitrary units.

Sensor signals 146, 148 indicate the passage of chain elements across a frame-fixed point located in the proximity of the force transmission trajectory. A chain element is any detectable part of the force transmission chain, such as a chain pin, a pin link or a supplemental detection element.

A frame-fixed point is a point fixed relative to a bicycle frame 130.

Let us assume that sensor signal 146 and sensor signal 148 illustrate chain detection in the front portion and the rear portion, respectively, of the force transmission trajectory. The front portion may be located in the proximity of the front force transmission contact point 122B while the rear portion may be located in the proximity of the rear force transmission contact point 122A.

FIG. 2 illustrates a case, where the tension of the power transmission chain 106 is low or moderate, thus resulting in first phase difference 144 between arbitrary parts of the force transmission chain 106. The phase difference may be expressed in angular units, in time units or in arbitrary units.

FIG. 3 illustrates a case, where the tension of the power transmission chain 106 is larger, thus resulting in second phase difference 150 between arbitrary parts of the force transmission chain 106. The change in phase difference indicates that a phase difference is a function of the stretching force 118, and thus the stretching force 118 may be obtained from the phase differences 144, 150.

In a real measurements situation, an arbitrary stretching force $F_a$ may be obtained from an arbitrary phase difference $\delta_a$ through the equation $$F_a = (\delta_a + \delta_g) \times K, \quad (4)$$

wherein K is a calibration constant characterizing the dependence between the stretching force 118 and the phase difference 150. Parameter $\delta_g$ is a gear-specific phase-offset, which transfer the phase calibration from a gear to another gear. The gear-specific phase offset arises from the difference in measurement geometry between different gears.

Let us assume that the first phase difference 144 represents a reference value for the phase difference if the corresponding stretching force 118 were known. In this case, the calibration constant reads $$K = \frac{F_1}{\delta_1}. \quad (5)$$

The reference force $F_1$ may be obtained from overall acceleration of the bicycle system $a_s$, the mass $m_s$ of the bicycle system comprising the bicycle and the cyclist, and the rear transmission ratio. In mathematical terms, an equation $$F_1 = a_s \times m_s \times A_{RTR} \quad (6)$$

may be applied.

In an embodiment of the invention, the reference force $F_1$ is obtained from a calibration procedure, where the cyclist is instructed to stand with full weight on a crank 102 while the crank 102 is being directed perpendicularly to the gravitation field. The bicycle may or may not be in motion. In this case, the reference force may be written as follows:

$$F_1 = m_c \times g \times A_{FTR} \quad (7)$$

wherein $m_c$ is the total mass of the cyclist, g is the gravitational acceleration ($\approx 9.81$ ms$^{-2}$), and $A_{FTR}$ is a front transmission ratio characterizing the length of the crank 102 relative to the radius of the front sprocket 104.

Figure 4:
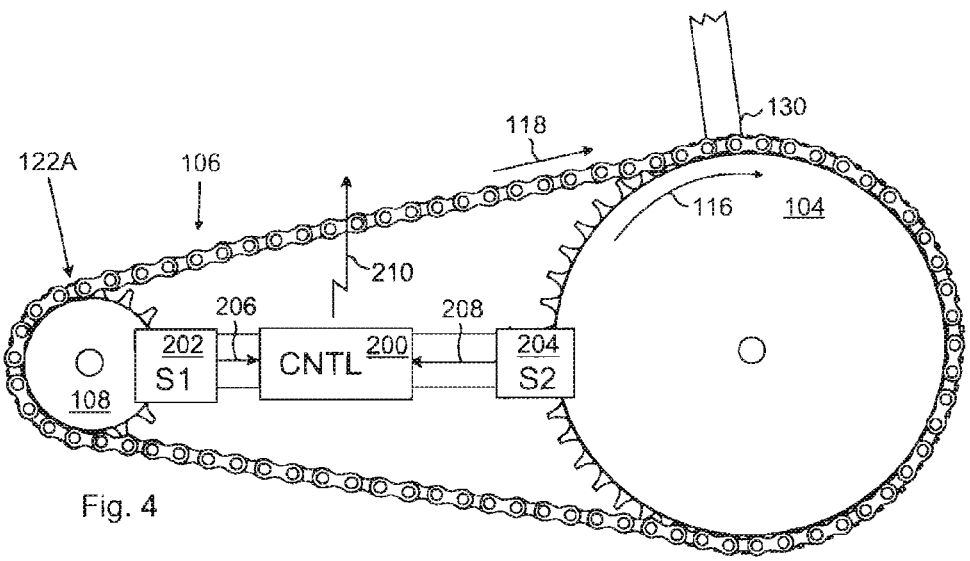
FIG. 4 shows a system for determining pedaling effort of a bicycle according to an embodiment of the invention.

FIG. 4 illustrates a system comprising a rear detector (S1) 202, a front detector (S2) 204, and a controller 200.

In an embodiment shown in FIG. 4, the rear detector 202 may be installed in the proximity of the rear sprocket 108 and generates a rear sensor signal 206 when a tooth of the rear sprocket 108 passes the rear detector 202. As the rear sprocket 108 and the force transmission chain 106 are locked into the same phase, the sensor signal 206 generated by the rear sprocket 108 indicates the passage of the transmission chain 106 across the rear frame-fixed point located at the rear force transmission contact point 122A.

In an embodiment of the invention, the front detector 204 generates a front sensor signal 208 when a tooth of a front sprocket 104 passes the front detector 204. In this case, the front sensor signal 208 indicates passage of the transmission chain 106 across the second frame-fixed point located at the front force transmission contact point 122B.

The controller 200 receives the rear sensor signal 206 and the front sensor signal 208 and determines a pedaling parameter proportional to tension of the force transmission chain 106 by using the rear sensor signal 208 and the front sensor signal 208.

Figure 5:
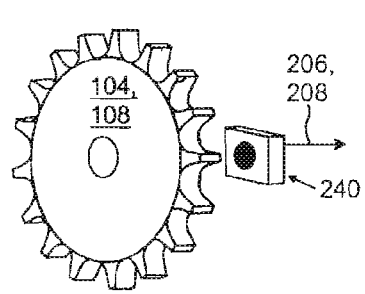
FIG. 5 shows a sensor element according to an embodiment of the invention.

An embodiment of a measurement configuration with a detection element 240 is shown in FIG. 5. The measurement configuration may be applied to the rear detector 202, front detector 204 or both the rear detector 202 and the front detector 204.

In an embodiment of the invention, the detection element 240 is an inductive element with a coil and possibly a magnetic core. The coil may be circular and oriented so that the magnetic field is parallel to the rotation axis of the sprocket 104, 108. In this configuration, the magnetic field is dynamically affected when the teeth of the rear and/or front sprocket move in the magnetic field.

In an embodiment of the invention, the detection element 240 is an optical element, a capacitive element or an audio element.

Figure 6:
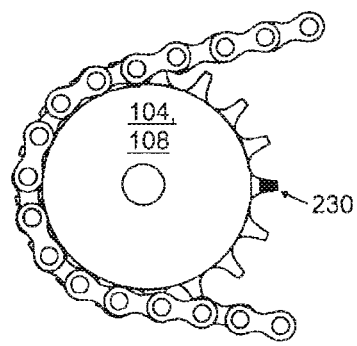
FIG. 6 shows a sprocket according to an embodiment of the invention.

With reference to FIG. 6, a sprocket 104, 108 comprises a reference tooth 230 which is equipped with an indicating structure, such as a magnetic component which acts as an identifier for the tooth. The indicating structure may be used for identifying a complete revolution of the sprocket 104, 108. A reference tooth may be applied in the rear sprocket 108, front sprocket 104 or in both the rear sprocket 108 and the front sprocket 104.

Figure 7:
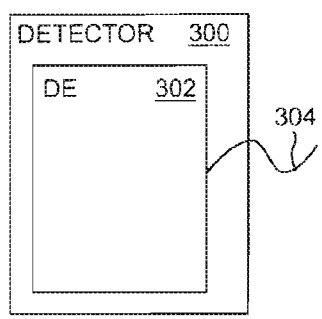
FIG. 7 shows a sensor according to an embodiment of the invention.

With reference to FIG. 7, a detector 300 may comprise a detection element 302 which is coupled to the controller 200 with a wire 304.

The detector 300 may be used as a rear detector 202, a front detector 204 or both as a rear detector 202 and a front detector 204.

Figure 8:
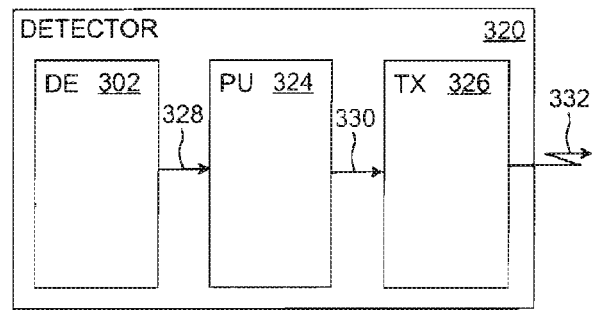
FIG. 8 shows a sensor according to an embodiment of the invention.

With reference to FIG. 8, a detector 320 may comprise a detection element 302, a processing unit 324 and a transmitter 326.

The detector 320 may be used as a rear detector 202, a front detector 204 or both as a rear detector 202 and a front detector 204.

The detection element 302 detects the passage of the transmission chain 106 in a frame-fixed point. A detection signal 328 is inputted into the processing unit 324.

The detection signal 328 may be similar to sensor signals 146, 148 shown in FIGS. 2 and 3.

The processing unit 324 receives the detection signal 328 and processes the detection signal 328.

In an embodiment of the invention, the processing unit 324 comprises a threshold level detector which indicates if the detection signal 328 exceeds a threshold level. The processing unit 324 may time stamp the threshold indication and include the time stamp into a result signal 330.

Let us assume that the rear sensor signal 146 and the front sensor signal 148 are time stamped with timing instants $T_r$ and $T_f$, respectively, as follows $$T_r = T_{rR} + T_{rI} \quad (8)$$

$$T_f = T_{fR} + T_{fI} \quad (9)$$

where $T_{rR}$ and $T_{rR}$ are reference time in the rear detector and the front detector, respectively. Time instants $T_{rI}$ and $T_{fI}$ are time stamps of the threshold indication in the rear detector and the front detector, respectively, relative to the reference times $T_{rR}$ and $T_{rR}$.

The time stamps may be included into result signal 330 which is fed into the transmitter 326. The transmitter 326 may encode the result signal 330 into a sensor signal 332 which may be transmitted wirelessly to the controller 200.

In a calibration procedure, the relative phase of the rear sensor signal and the front sensor signal may be obtained from the equation $$\delta_1 = T_f - T_r \quad (10)$$

Equation (10) indicates that in the phase difference detection, reference times $T_{rR}$ and $T_{rR}$ cancel out, and the phase difference at an arbitrary phase may be determined provided that the reference clocks are synchronized with sufficient accuracy.

In an embodiment of the invention, the processing unit 324 transforms the sensor signal 328 into digital form. A digitized sensor signal may be included into the result signal 330 and transmitted wirelessly to the controller 200.

The sensor signal 332 may be a digital signal comprising a frame structure with sensor identification code and time stamp information.

Figure 9:
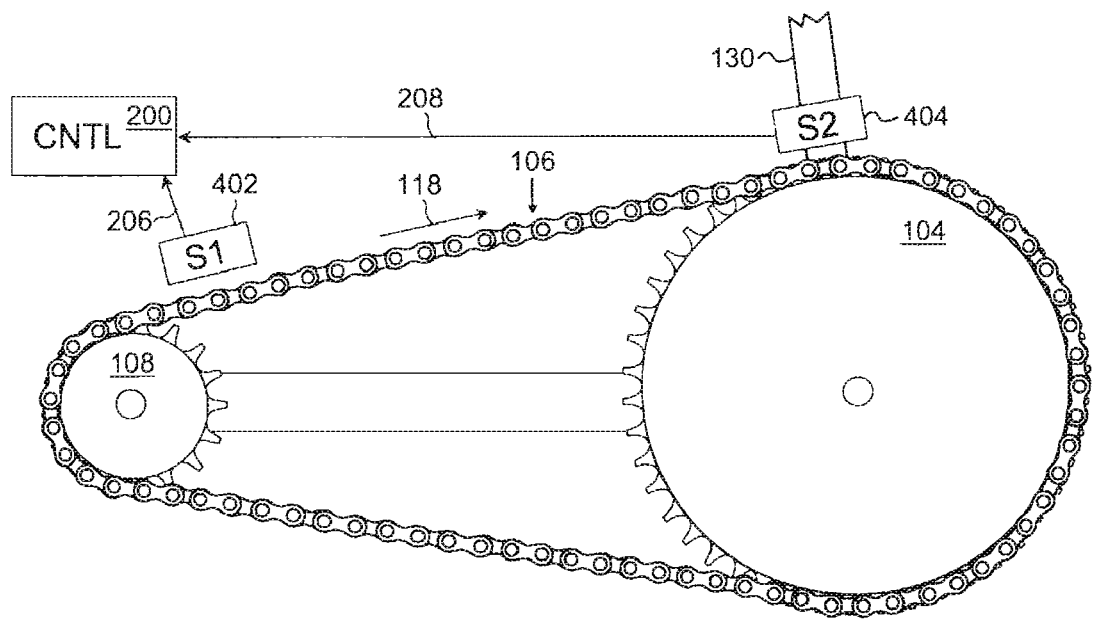
FIG. 9 shows a system for determining pedaling effort of a bicycle according to an embodiment of the invention.

With reference to FIG. 9, the rear detector 402 may be installed so as to detect a signal as a response to the force transmission chain 106 passing the rear detector 402. The detection is based on regular structure variation in the chain structure which is due to pins and pin links, for example.

The rear detector 402 may be fixed to a rear fork not shown in FIG. 7. The distance of the rear detector 402 from the force transmission chain 106 may vary from 1 centimeter to 3 centimeters, for example, thus enabling variation in the force transmission trajectory due to different sprockets in a sprocket cluster. The rear detector 402 may be based on inductive, capacitive or optical sensing.

In an embodiment of the invention, the front detector 404 is installed so as to detect a signal as a response to the force transmission chain 106 passing the front detector 404.

The front detector 404 may be fixed to a frame beam 130. The distance of the front detector 404 from the force transmission chain 106 vary from 1 centimeter to 3 centimeters. The front detector 402 may be based on inductive, capacitive or optical sensing.

In an embodiment of the invention, the front detector 404 is further applied for sensing the passage of the crank 102, thus enabling pedaling cadence to be detected in the controller 200. In such a case, the front sensor signal 208 may include cadence information.

Figure 10:
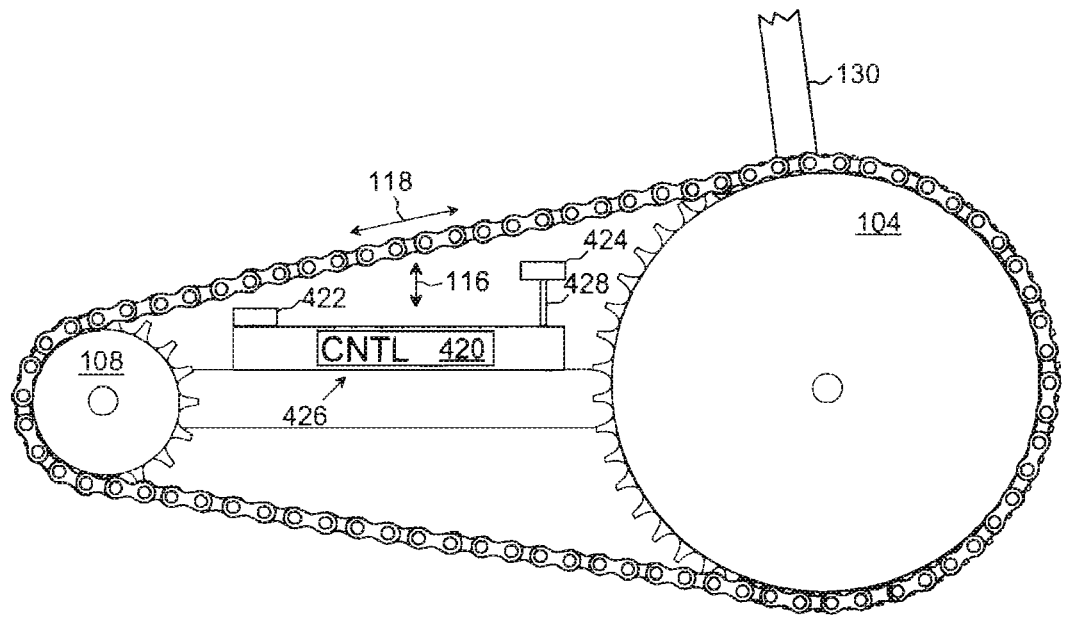
FIG. 10 shows a system for determining pedaling effort of a bicycle according to an embodiment of the invention.

With reference to FIG. 10, the rear detector 422, the front detector 424 and the controller 420 are integrated so as to form a compact structure 426.

The compact structure 426 may be attached to the rear fork of the bicycle, for example.

The rear detector 422 and/or the front detector 424 may be attached to the body of the compact structure 426 by extensions 428 which may be flexible. The extensions 428 enable the rear detector 422 and the front detector 424 to be adjusted according to the physical dimensions of the bicycle.

In an embodiment of the invention, the system further comprises a vibration detector configured to detect vibration of the force transmission chain, wherein the vibration is perpendicular to the force transmission trajectory. The detector may be a separate element, or it may be integrated with a detector 402, 404, 422, 424.

Figure 11:
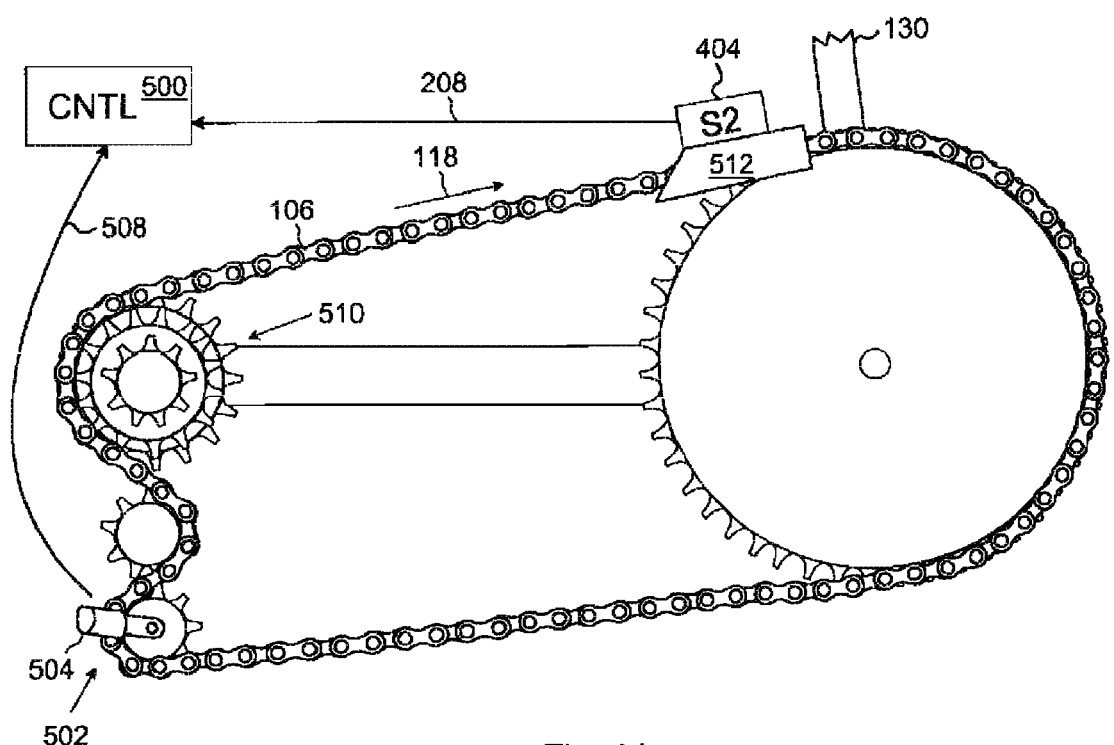
FIG. 11 shows a system for determining pedaling effort of a bicycle according to an embodiment of the invention.

With reference to FIG. 11, the rear detector is implemented with a jockey wheel detector 504 which may be attachable to a rear gear shift mechanism 502. The jockey wheel detector 504 follows the rear gear shift mechanism 502 when the rear gear is shifted, thus preserving a measurement geometry regardless of the rear gear. The jockey wheel detector 504 may be based in inductive, capacitive, optic or audio sensing.

In an embodiment of the invention, the front detector 404 is attachable to a front gear shift mechanism 512. The front detector 404 follows the front gear shift mechanism 512 when the front gear is shifted, thus preserving a measurement geometry regardless of the front gear. The front detector 404 may be based on inductive, capacitive, optic or audio sensing.

The front detector 404 may also be implemented with any of the embodiments shown in FIG. 4, 9 or 10.

A rear detector 202, 402, 422 and/or 504 may be implemented with detector structures shown in FIGS. 7 and 8.

A front detector 204, 404 and/or 424 may be implemented with detector structures shown in FIGS. 7 and 8.

Figure 12:
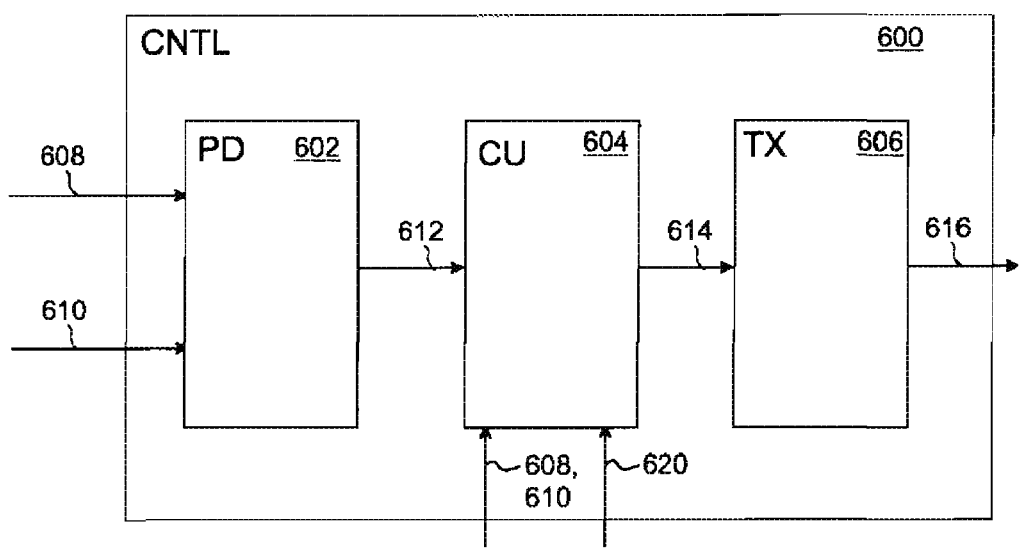
FIG. 12 shows a controller for determining pedaling effort of a bicycle according to an embodiment of the invention.

With reference to FIG. 12, the controller 600 may comprise a phase detector 602, a calculation unit 604 and a transmitter 606.

The phase detector 602 receives the rear sensor signal 608 from the rear detector 202, 402, 422, 504 and the front sensor signal 610 from the front detector 204, 404, 424.

The phase detector 602 determines the relative phase of the rear sensor signal 608 and the front sensor signal 610.

In an embodiment of the invention, the phase detector 602 calculates a correlation between the rear sensor signal 608 and the front sensor signal 610. The correlation is high when the phase difference of the force transmission chain at the rear detector 202, 402, 422, 504 and at the front detector 204, 404, 424 is small. The correlation is small when the phase difference of the force transmission chain 106 at the rear detector 202, 402, 422, 504 and at the front detector 204, 404, 424 is large.

The correlation may be calculated with a digital signal processor. In this case, the phase detector 602 may comprise an analogue-to-digital converter for converting rear sensor signal 608 and the front sensor signal 610 from the analogue domain into the digital domain.

In an embodiment of the invention, the phase detector 602 comprises an amplifier, a threshold detector and a counter. The amplifier amplifies an initial signal, such as that shown in FIG. 2 or 3, thus generating steep clock edges. The amplified signal is inputted into the threshold detector which detects a threshold of the clock edge and starts a counter, such as a 32 kHz clock. The counter counts clock signals until a clock edge of another signal stops counting. A counter output characterizes the phase difference between the two signals.

In an embodiment, the sensor signals 608, 610 are digital signals comprising time stamps generated in a detector similar to that described with conjunction of FIG. 8. In such as case, the phase detector 602 detects the phase difference by using the time stamps.

The phase detector 602 outputs phase difference information 612 to the calculation unit 604 which calculates a parameter proportional to the tension of the force transmission chain 106.

In an embodiment of the invention, the calculation unit 604 calculates the stretching force 118 of the force transmission chain 106. The calculation unit 604 may comprise a memory unit for storing calibration information, such as the calibration constant K and transmission parameters, such as the rear transmission ratio and the front transmission ratio. A calculation formula similar to that shown in equation (4) may be used for calculating the stretching force 118 in a digital processor of the calculation unit 604.

In an embodiment of the invention, the memory unit of the calculation unit 604 includes a register for storing information on rear and/or front sprocket clusters. The register may include the number of teeth of each sprocket and/or the gear-specific phase-offset.

In an embodiment of the invention, the calculation unit 604 receives rear sensor signal 608 and/or the front sensor signal 610 and calculates the velocity of the force transmission chain 106 by using the rear sensor signal 608 and/or the front sensor signal 610. Also, the calculation unit may comprise a register which includes chain-specific information, such as the length of a pin link $l_{pl}$ which is typically 12.7 millimeters. The velocity $v_{ch}$ of the force transmission chain may be obtained from the equation $$v_{ch} = l_{pl} \times f_{pl}, \quad (11)$$

wherein $f_{pl}$ is half of the frequency of the rear sensor signal 608 and/or the front sensor signal 610.

In an embodiment of the invention, the calculation unit 604 calculates the pedaling power by using the phase difference information 612 and the chain velocity $v_{ch}$ by using equations (2) and (4), for example.

In an embodiment of the invention, the calculation unit 604 receives speed information signal 620 characterizing the speed of the bicycle. The speed information signal may 620 be provided by the motion sensing system described above.

In an embodiment of the invention, the calculation unit 604 detects a gear and applies the gear-specific phase offset when determining the pedaling parameter. A gear detection may be based on comparison between the chain velocity and the overall bike velocity.

In an embodiment of the invention, the calculation unit 604 executes a calibration algorithm by determining the acceleration of the bicycle and a corresponding phase difference at the rear sensor 202, 402, 422, 504 and the front sensor 204, 404, 424. In an embodiment, the acceleration of the bicycle is determined from the time dependence of the speed information signal 620.

In an embodiment of the invention, the calculation unit 604 determines chain acceleration $a_{ch}$ by using the time dependence of the chain velocity $v_{ch}$. In such a case, the calculation unit 604 may calculate the calibration constant by using the chain acceleration and mass of the bicycle system from the equation $$K = \frac{a_{ch} \times m_s}{\delta_1}. \quad (13)$$

In an embodiment of the invention, the calculation unit 604 determines a pedaling parameter by using the perpendicular vibration of the force transmission chain. The pedaling parameter may be pedaling force and/or pedaling power. In an embodiment of the invention, the pedaling force and/or pedaling power is used for determining the calibration constant K.

In an embodiment of the invention, the calculation unit 604 calculates a correction parameter for correcting the pedaling power and/or pedaling force obtained from the vibration measurement. The calculation unit 604 may for example determine higher order terms, such as k' and k" shown in equation (1).

The calculation unit 604 may feed pedaling effort signal 614 into the transmitter 606. The pedaling effort signal 614 includes information on the pedaling effort, such as pedaling power and/or pedaling force. The pedaling effort signal 614 may further include cadence information, chain speed information and/or chain acceleration information.

In an embodiment of the invention, the transmitter 606 generates a carrier wave 616 which transmits the contents of the pedaling effort signal 614 into a bike computer, for example.

The phase detector 602 may be implemented with a computer program executable in a digital processor and stored in a memory. In an embodiment of the invention, the phase detector 602 is implemented with ASIC (application-specific-integrated circuit).

The calculation unit 604 may be implemented with a computer program executable in a digital processor and stored in a memory. In an embodiment of the invention, the calculation unit is implemented with ASIC.

The transmitter 606 may be implemented a computer program executable in a digital processor and stored in a memory and radio frequency ASIC. In an embodiment, the transmitter 606 applies magnetic transmission implemented with a coil, for example.

The controller 600 may comprise attaching mechanism with which the controller 600 may be mounted to the bike frame.

Figure 13:
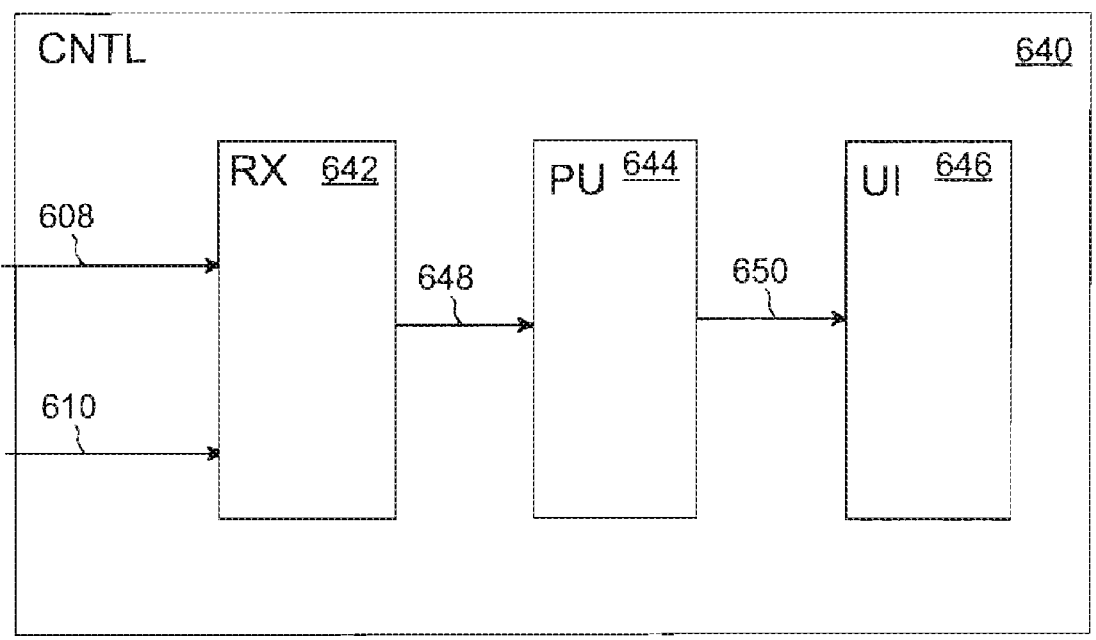
FIG. 13 shows a controller for determining pedaling effort of a bicycle according to an embodiment of the invention.

With reference to FIG. 13, the controller 640 may comprise a receiver 642, processing unit 644 and a user interface 646.

In an embodiment of the invention, the receiver 642 receives the rear sensor signal 608 and the front sensor signal 610 and inputs data 648 on the rear sensor signal 608 and the front sensor signal 610 into the processing unit 644.

In an embodiment of the invention, the processing unit 644 implements the phase detection unit 602.

In an embodiment of the invention, the processing unit 644 implements the calculation unit 604.

In an embodiment of the invention, the processing unit 644 provides pedaling effort signal 650 to the user interface 646 which shows the pedaling power and/or pedaling force to the user. The user interface 646 may comprise a display and an input device, such as a keypad.

Computer program elements described above may be stored on a computer program distribution medium readable by a computer or a processor. The computer program medium may be, for example but not limited to, an electric, magnetic, optical, infrared or semiconductor system, device or transmission medium. The computer program medium may include at least one of the following media: a computer readable medium, a program storage medium, a record medium, a computer readable memory, a random access memory, an erasable programmable read-only memory, a computer readable software distribution package, a computer readable signal, a computer readable telecommunications signal, computer readable printed matter, and a computer readable compressed software package.

What is claimed is:

1. A system for determining pedaling effort of a bicycle, comprising:
    a first detector for generating a first sensor signal responsive to passage of a force transmission chain across a first frame-fixed point located in the proximity of the force transmission trajectory of the force transmission chain;
    a second detector for generating a second sensor signal responsive to passage of a force transmission chain across a second frame-fixed point located in the proximity of the force transmission trajectory of the force transmission chain; and
    a controller configured to receive the first sensor signal and the second sensor signal and configured to determine a first pedaling parameter proportional to tension of the force transmission chain on the basis of a phase difference between the first sensor signal and the second sensor signal.

2. The system according to claim 1, wherein the controller is further configured to detect the phase difference between the first sensor signal and the second sensor signal; and wherein the controller is further configured to determine a parameter proportional to tension on the basis of the phase difference.

3. The system according to claim 1, wherein the controller is further configured to calculate velocity of the force transmission chain by using the first sensor signal or the second sensor signal.

4. The system according to claim 1, wherein the controller is further configured to calculate acceleration of the force transmission chain by using the first sensor signal or the second sensor signal.

5. The system according to claim 3, wherein the controller is further configured to calculate tension of the force transmission chain, and wherein the controller is further configured to calculate pedaling power of the bicycle by using the tension and the velocity of the force transmission chain.

6. The system according to claim 4, wherein the controller is further configured to calibrate the first pedaling parameter by using the acceleration.

7. The system according to claim 1, wherein the first detector is configured to generate a first sensor signal responsive to a tooth of a rear sprocket passing the first detector, thereby indicating passage of the transmission chain across the first frame-fixed point located at the force transmission contact point between the force transmission chain and the rear sprocket.

8. The system according to claim 1, wherein the second detector is configured to generate a second sensor signal responsive to a tooth of a front sprocket passing the second detector, thereby indicating passage of the transmission chain across the second frame-fixed point located at the force transmission contact point between the force transmission chain and the front sprocket.

9. The system according to claim 1, wherein the first detector is configured to generate the first sensor signal as a response to the force transmission chain passing the first detector.

10. The system according to claim 1, wherein the second detector is configured to generate the second signal as a response to the force transmission chain passing the second detector.

11. The system according to claim 1, further comprising a vibration detector configured to detect vibration of the force transmission chain, wherein the vibration is perpendicular to the force transmission trajectory, wherein the controller is further configured to determine a second pedaling parameter by using the vibration, and wherein the controller is further configured to calculate a third pedaling parameter by using the first pedaling parameter and the second pedaling parameter.

12. A method of determining pedaling effort of a bicycle, comprising:
   generating a first sensor signal responsive to passage of a force transmission chain across a first frame-fixed point located in the proximity of the force transmission trajectory of the force transmission chain;
   generating a second sensor signal responsive to passage of a force transmission chain across a second frame-fixed point located in the proximity of the force transmission trajectory of the force transmission chain;
   receiving the first sensor signal and the second sensor signal; and
   determining a first pedaling parameter proportional to tension of the force transmission chain on the basis of a phase difference between the first sensor signal and the second sensor signal.

13. A non-transitory computer readable storage medium comprising encoded instructions that, when executed by a processing device, cause the processing device to:
   receive a first sensor signal responsive to passage of a force transmission chain across a first frame-fixed point located in the proximity of the force transmission trajectory of the force transmission chain;
   receive a second sensor signal responsive to passage of a force transmission chain across a second frame-fixed point located in the proximity of the force transmission trajectory of the force transmission chain; and
   determine a first pedaling parameter proportional to tension of the force transmission chain on the basis of a phase difference between the first sensor signal and the second sensor signal.

* * * * *